United States Patent
Zahlmann et al.

(10) Patent No.: US 7,283,653 B2
(45) Date of Patent: Oct. 16, 2007

(54) METHOD AND SYSTEM FOR SUPPORTING THE EVALUATION OF A PICTURE OF AN EYE

(75) Inventors: Gudrun Zahlmann, Neurmarkt (DE); Volker Schmidt, Erlangen (DE); Siegfried Schneider, Erlangen (DE)

(73) Assignee: Siemens Aktiengesellschaft, München ( * ) Notice: Subject to any disclaimer, the term of this patent is extended or adjusted under 35 U.S.C. 154(b) by 965 days.

(21) Appl. No.: 10/305,036

(22) Filed: Nov. 26, 2002

(65) Prior Publication Data
US 2004/0102682 A1    May 27, 2004

(51) Int. Cl.
    *G06K 9/00* (2006.01)
(52) U.S. Cl. ...................... 382/128; 600/300
(58) Field of Classification Search .............. 382/128, 382/129, 130, 131, 132, 133, 134, 117; 351/221, 351/205, 214; 600/300, 400–408, 710, 318, 600/358, 476, 558
See application file for complete search history.

(56) References Cited

U.S. PATENT DOCUMENTS

| 5,943,116 A * | 8/1999 | Zeimer | 351/221 |
| 6,179,421 B1 * | 1/2001 | Pang | 351/205 |
| 6,631,990 B2 * | 10/2003 | Schippert et al. | 351/214 |
| 2001/0005427 A1 * | 6/2001 | Takemoto | 382/162 |
| 2002/0052551 A1 * | 5/2002 | Sinclair et al. | 600/476 |

FOREIGN PATENT DOCUMENTS

| WO | WO 96/13790 | 5/1996 |
| WO | WO 02/084511 A1 | 10/2002 |

OTHER PUBLICATIONS

Printout from Website http:/www.diabetic-retinopath.scr.ng.nhs.uk/diabetic-retinopath.html.
"Hybrid Fuzzy Image Processing For Situation Assessment," Zahlmann et al, IEEE Engineering In Medicine and Biology, Jan./Feb. 2000, pp. 76-83.

* cited by examiner

*Primary Examiner*—Samir Ahmed
*Assistant Examiner*—Abolfazl Tabatabai
(74) *Attorney, Agent, or Firm*—Alexander J. Burke (57) ABSTRACT

In a method and a system for supporting the evaluation of a picture of a patient's eye the picture is displayed on a screen. An image-processing algorithm from a number of image processing algorithms is selected due to a preliminary diagnosis selected from a number of diagnoses which are related to diabetes. Each image-processing algorithm of the number of image processing algorithms is associated with a diagnosis of the number of diagnoses and is designed to search for a pattern which is specific to the respective diagnosis. The selected image-processing algorithm then is applied to the picture and a pattern which is detected by the selected image-processing algorithm is marked on the screen in the picture.

16 Claims, 5 Drawing Sheets

METHOD AND SYSTEM FOR SUPPORTING THE EVALUATION OF A PICTURE OF AN EYE

BACKGROUND OF THE INVENTION

1. Field of the Invention

The invention relates to methods and systems for supporting the evaluation of a picture of an eye.

2. Description of the Prior Art

According to the UK National Screening Committee's (NSC) web site (http://www.diabetic-retinopathy.screening.nhs.uk) approximately 2% of the UK population are known to have diabetes, of whom 200,000 have Type 1 diabetes, and more than a million have type 2 diabetes. This number is expected to increase. It has been estimated that the prevalence of type 2 diabetes in the UK will more than double between 1997 and 2010.

One complication of diabetics is diabetic retinopathy which may affect the blood vessels of the retina. Growth of new blood vessels, known as proliferative retinopathy, may lead to blindness through hemorrhage and scarring. A deterioration of retinal blood vessels causing loss of blood vessels and leakage into the retina is known as maculopathy and leads to visual impairment and may progress to blindness.

Diabetic retinopathy is the biggest single cause of registered blindness in the UK among working age people. Significantly greater numbers suffer visual impairment and handicap due to the effects of diabetic retinopathy. Blindness can cause loss of earning capacity in working age people and required social support is significant, potentially outweighing the costs of prevention and treatment. Diabetic retinopathy can be treated, for instance, by tight glycaemic control and tight blood pressure control. Both treatments reduce the development and progression of diabetic retinopathy in type 1 and type 2 diabetes. In order to be treated, diabetic retinopathy must be diagnosed as soon as possible.

Thus, the need to screen for diabetic retinopathy is uncontroversial. For the screening, images of the eyes of a group of persons who are diagnosed with diabetes are taken and subsequently evaluated. The images may be evaluated by a grader who may be ophthalmologist, a general practitioner, or a person without or hardly any medical background. The grader evaluates the image of the eye by searching for typical patterns related to specific complications due to diabetes.

SUMMARY OF THE INVENTION

An objective of the present invention is to provide methods which support the evaluation of the picture of a patient's eye.

Another objective of the present invention is to provide a system which support the evaluation of the picture of a patient's eye.

The first objective is achieved in accordance with the invention in a method for supporting the evaluation of a picture of an eye, including the steps of: displaying a picture of a patient's eye on a screen, determining a series of regions of interest in the picture, and subsequently marking each region of interest in the picture. The series of regions of interest is adapted to a person selected from the group of persons who are evaluating the series of regions in the picture.

According to the inventive method, the picture of the patient's eye will be evaluated. The picture may be taken during a screening of a plurality of patients who are diagnosed with diabetes. The picture is particularly taken from the patient's retina. Patients having diabetes are prone to develop certain eye-related abnormalities, so called lesions, or diseases which may lead to blindness. Such eye-related lesions or diseases include micro-aneurysms, background/non-proliferative (mild/moderate) retinopathy, post treatment quiescent, maculopathy, clinical significant macular oedema (CSMO), pre-proliferative retinopathy, proliferative retinopathy, and advanced diabetic eye disease. In order to diagnose a patient with at least one of the eye- and diabetic-related eye diseases, a doctor or a trained person with little or no medical background, a so called grader, evaluates a picture of the patient's eye and searches for patterns specific to the relevant eye-disease. For instance, if the patient has background/non-proliferate retinopathy, then the patient's eye may have so called cotton wool spots, hemorrhages, and/or hard exudates plus their location in relation to the temporal arcade per eye.

For the diagnosis, some graders or doctors may examine subsequently certain regions of the eye, so called regions of interest. Thus, according to the inventive method, the series of regions of interest is adapted to the person who evaluates the picture.

In order to determine the series of regions of interest, the series is determined during a learning mode according to a further embodiment of the invention.

In a further embodiment of the inventive method, at least one region of interest of the series of regions of interest may be surrounded by a frame.

In a preferred embodiment of the inventive method, at least one relevant region of interest is determined by selecting an image processing algorithm from a plurality of image processing algorithms, applying the selected image processing algorithm to the picture, and marking a detected pattern as the relevant region of interest. The selected image-processing algorithm is designed to detect a pattern which is related to said at least one region of interest.

The detected pattern may be emphasized in accordance with one embodiment of the inventive method.

The first objective also is achieved in accordance with the invention in a method for supporting the evaluation of a picture of an eye, including the steps of displaying a picture of a patient's eye and selecting an image processing algorithm from a number of image-processing algorithms based on a preliminary diagnosis selected from a number of diagnoses which are related to diabetes, applying the selected image processing algorithm to the picture, and marking a pattern which is detected by the selected image processing algorithm in the picture. Each image-processing algorithm in the number of image processing algorithms is associated with a diagnosis of the number of diagnoses and is designed to search for a pattern which is specific to the relevant diagnosis.

Some doctors or graders may prefer to first make a preliminary diagnosis and then to verify the preliminary diagnosis by searching for the related lesions in the picture. Each lesion has a specific pattern. Thus, if the doctor or grader finds a pattern associated with the relevant lesion, then the preliminary diagnosis is verified. If the preliminary diagnosis is, for instance, background/non-proliferate retinopathy, then the picture comprises cotton wool spots, hemorrhages, and/or hard exudates plus their location in relation to the temporal arcade per eye.

If the preliminary diagnosis is, for instance, background/non-proliferate retinopathy, then the selected image processing algorithm is designed to detect patters which are typical for cotton wool spots, hemorrhages, and/or hard exudates plus their location in relation to the temporal arcade per eye. Suitable image processing algorithms are, for instance, disclosed in G. Zahlmann, et al, "Hybrid Fuzzy Image Processing For Situation Assessment", IEEE Engineering In Medicine And Biology, January/February 2000, pp. 76-83.

The detected pattern may be emphasized or surrounded by a frame in accordance with preferred embodiments of the inventive method.

The second objective is achieved in accordance with the invention in a system having a database, a screen, and a data processing unit which is operatively coupled to the screen and to the database. The database contains a number of pictures of the eyes of a number of patients who are diagnosed with diabetes. The data processing unit is configured to retrieve a picture selected from the number of pictures from the data base, display the retrieved picture on the screen, determine a series of regions of interest in the retrieved picture, and subsequently mark each region of interest of the series of regions of interest in the picture. The series of regions of interest is adapted to a person selected from group of persons who are evaluating pictures in the number of pictures.

The second objective is also achieved in accordance with the invention in a system having a database, a screen, and a data processing unit which is operatively coupled to the screen and to the database. The database contains a number of pictures of the eyes of a number of patients who are diagnosed with diabetes. The data processing unit is configured to retrieve a picture selected from the number of pictures from the data base, display the retrieved picture on the screen, select an image processing algorithm from a number of image-processing algorithms, apply the selected image processing algorithm to the picture, and mark a detected pattern in the retrieved picture. The selected image-processing algorithm is designed to detect a pattern which is related to a preliminary diagnosis selected from a number of diagnoses.

DESCRIPTION OF THE PREFERRED EMBODIMENTS

Figure 1:
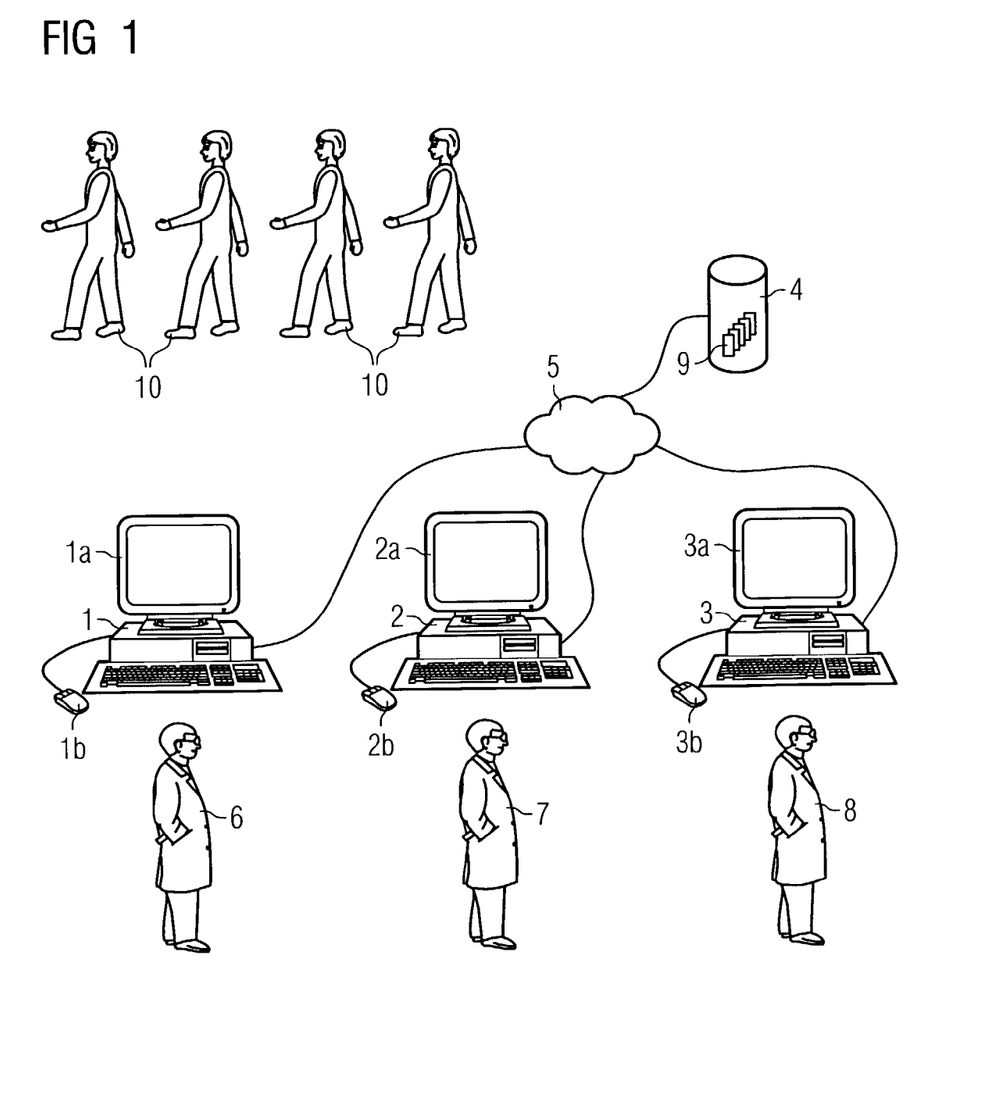
FIG. 1 shows a scenario illustrating the invention.

FIG. 1 illustrates an example of the inventive system. The system comprises computers 1 to 3 which are operatively connected to a database 4 over an information network 5. The database 4 has pictures 9 which were taken from the eyes (retinas) of a group of patients 10. Each patient of the group of patients 10 is diagnosed with diabetes.

In the present embodiment, graders 6 to 8 evaluate the pictures 9 using the computers 1 to 3. If one of the graders 6 to 8 wants to evaluate one of the pictures 9, then she/he logs on on one of the computers 1 to 3 and retrieves one of the pictures 9 from the database 4 with the respective computer. When the relevant picture is retrieved, then it is displayed on a screen which is connected to the relevant computer. In order to retrieve a picture from the database 4, the database 4 and the computers 1 to 3 are configured accordingly. Such configurations are well known in the art and thus need not be further explained.

Figure 2:
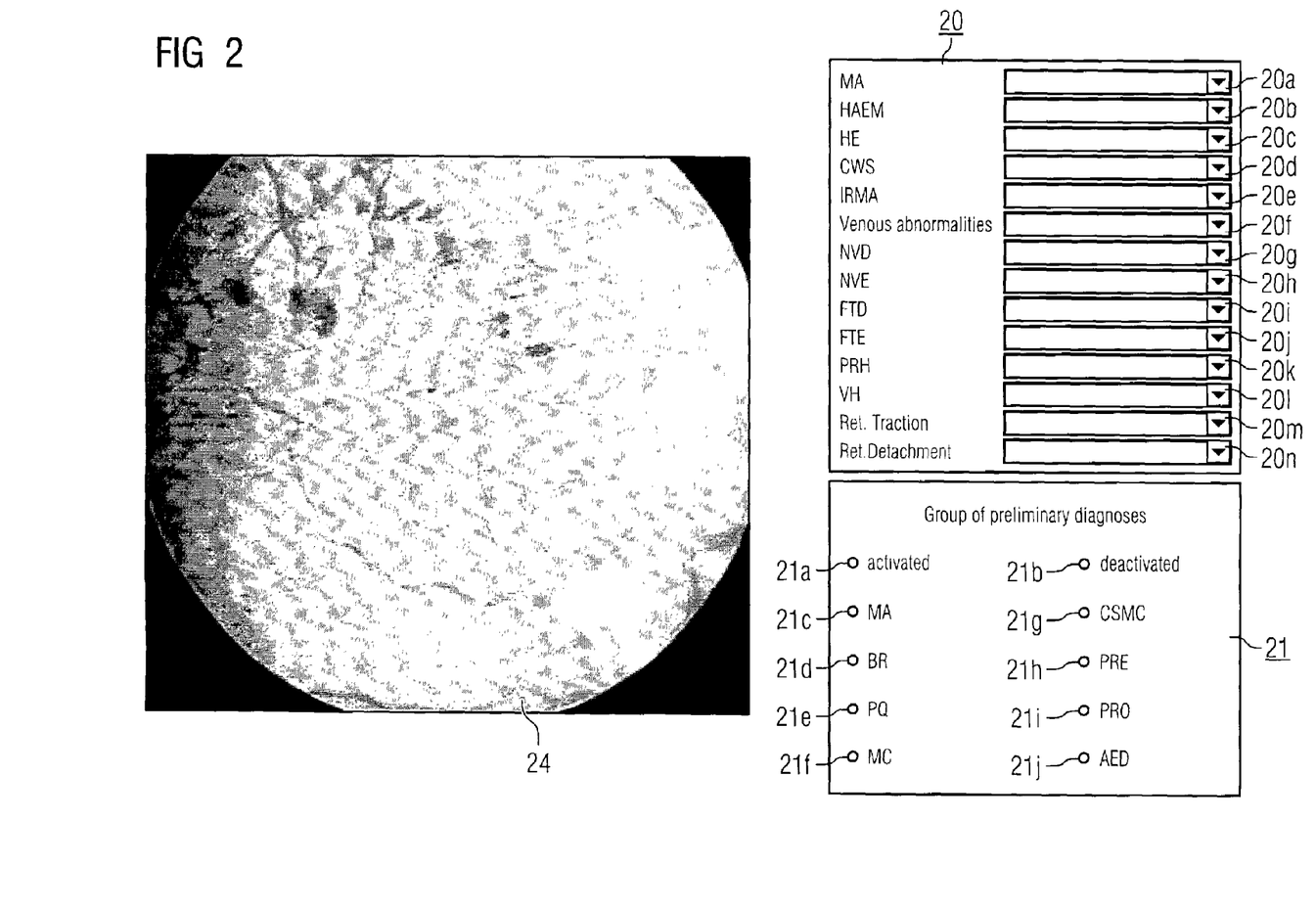
FIG. 2 shows a picture of a patient's eye.

FIG. 2 depicts an example of one of the pictures 4 which has been retrieved from the database 4 and is displayed on one of the screens 1a to 3a. The displayed picture has a reference sign 24. In order to document the evaluation of a displayed picture, a list 20 which comprises several pull-down menus 20a to 20n and a list 21 which comprises several radio buttons 21a to 21l are displayed in addition to the picture 24 on the relevant screen in the present example. Each pull-down menu of the list 20 is related to a specific lesion which can appear in an eye. In the present embodiment, the relevant grader documents a micro-aneurysm (MA) with the pull-down menu 20a, hemorrhages (HAEM) with the pull-down menu 20b, hard exudates (HE) with the pull-down menu 20c, cotton wool spots (CWS) with the pull-down menu 20d, intra-retinal microvascular abnormalities (IRMA) with the pull-down menu 20e, venous abnormalities with the pull-down menu 20f, a neovascularization on optic disc (NVD) with the pull-down menu 20g, a neovascularization elsewhere (NVE) with the pull-down menu 20h, a fibrous tissue on optic disc (FTD) with the pull-down menu 20i, a fibrous tissue elsewhere (FTE) with the pull-down menu 20j, pre-retinal hemorrhages (PRH) with the pull-down menu 20k, vitreous hemorrhages (VH) with the pull-down menu 20l, a retinal traction with the pull-down menu 20j, and a retinal detachment with the pull-down menu 20n.

Some graders prefer to evaluate a picture according to a preliminary diagnosis. The relevant grader may make the preliminary diagnosis by giving a displayed picture a quick glance or the preliminary diagnosis may be made by somebody else before the retrieval of the relevant picture. During the evaluation, the relevant grader tries to verify the preliminary diagnosis by searching for the relevant lesions in the relevant picture. In order to support those grader, the list 21 is displayed in the present example. Using the radio buttons 21a to 21j, the grader can make a preliminary diagnosis selected from a group of preliminary diagnoses. Alternatively, a preliminary diagnosis may already be selected before retrieving the relevant picture from the database 4. A preliminary diagnosis can be selected by activating the radio button 21a and one of the radio buttons 21c to 21. In the present example, the group of preliminary diagnoses comprises "microaneurysms" (MA), "background/non-proliferative (mild/moderate) retinopathy" (BR), "post treatment quiescent" (PQ), "maculopathy" (MC), "clinical significant macular oedema" (CSMO), "pre-proliferative retinopathy" (PRE), "proliferative retinopathy" (PRO), and "advanced diabetic eye disease" (AED). Consequently, the preliminary diagnosis "microaneurysms" (MA) is selected by activating the radio button 21c, the preliminary diagnosis "background/non-proliferative (mild/moderate) retinopathy" (BR) is selected by activating the radio button 21d, the preliminary diagnosis "post treatment quiescent" (PQ) is selected by activating the radio button 21e, the preliminary diagnosis "maculopathy" (MC) is selected by activating the radio button 21f, the preliminary diagnosis "clinical significant macular oedema" (CSMO) is selected by activating the radio button 21g, the preliminary diagnosis "pre-proliferative retinopathy" (PRE) is selected by activating the radio button 21h, the preliminary diagnosis "proliferative retinopathy" (PRO) is selected by activating the radio button 21i, and the preliminary diagnosis "advanced diabetic eye disease" (AED) is selected by activating the radio button 21j. If a grader does not want to evaluate a picture based on a preliminary diagnosis, then she/he can deactivate the list 21 by activating the radio button 21b. A radio button can be activated with a mouse 1b which is connected to the computer 1, a mouse 2b which is connected to the computer 2, and a mouse 3b which is connected to the computer 3.

Some graders prefer to evaluate a displayed picture by subsequently searching for lesions in different regions of the eye. For example, some graders prefer to first evaluate the macula and then the periphery of the eye's disk. The relevant grader may mark the relevant region of the displayed eye, for instance by surrounding it using the mouse which is connected to the relevant computer, and then zoom in the marked region.

In order to meet the individual preference of each grader 6 to 8, the computers 1 to 3 are configured to support each grader by her/his evaluation individually. In the present example, the computers 1 to 3 are configured to learn the individual habits of the graders 1 to 3 during a learning mode.

In the present embodiment, the grader 6 prefers to evaluate a displayed picture based on a preliminary diagnosis. Thus, if she/he logs onto one of the computers 1 to 3 during the learning mode and retrieves one of the pictures 9 from the database 4 with the computer she/he is logged on, then she/he activates the radio button 21a of the list 21 and selects one of the preliminary diagnoses. Since the grader 6 usually activates the list 21 of the group of preliminary diagnoses, the computers 1 to 3 learn this habit during the learning mode. As a result, the list 21 of the preliminary diagnoses is already activated when the grader 6 retrieves a picture from the database 4 during an operating mode.

In the present embodiment, the grader 7 prefers to deactivate the list 21 of preliminary diagnoses and to evaluate a retrieved picture by first evaluating the macula and then the periphery disk of the displayed eye. During the learning mode, she/he therefore subsequently deactivates the list 21 of preliminary diagnoses, marks the macula of the displayed eye by surrounding the relevant region with a frame, zooms in the marked region, evaluates the macula, zooms out the marked region, and marks the periphery disk of the displayed eye. The computers 1 to 3 learn this habit during the learning mode. During the operating mode, the relevant computer automatically deactivates the list 21 of preliminary diagnoses, marks the macula of the displayed eye and zooms in the marked macula, when the grader 7 retrieves one of the pictures 9 from the database 4. When the grader 7 zooms the marked macula out, the relevant computer marks the periphery disk of the displayed eye.

In the present exemplary embodiment, grader 8 prefers to evaluate a picture based on a preliminary diagnosis and to subsequently search for lesions in different regions of the eye. The computers 1 to 3 learn the grader's 8 habit during the learning mode. During the operating mode, the relevant computer automatically activates the list 21 of the group of preliminary diagnoses and marks regions of a displayed eye in accordance with the grader's 8 preference, as soon as she/he retrieves a picture from the database 4.

Figure 3:
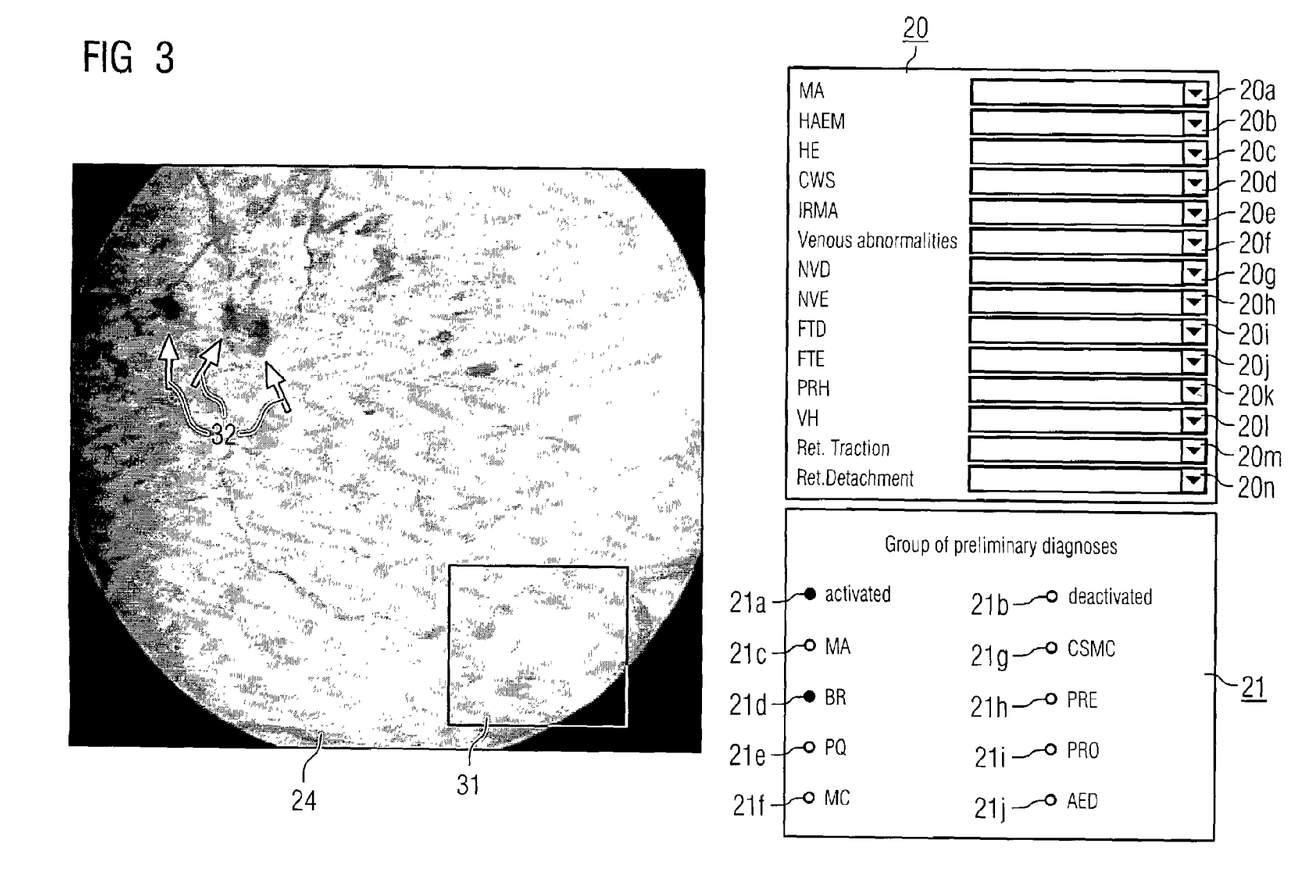
FIG. 3 to FIG. 5 show pictures whose displays are adapted to different persons.

In the present example, the grader 6 is logged on the computer 1 during the operating mode. If she/he retrieves the picture 24 from the database 4, then the picture 24 is displayed on the screen 1a and the radio button 21a of the list 21 of the group of preliminary diagnoses is automatically activated, as shown in FIG. 3. After that, the grader 6 makes a preliminary diagnosis "background/non-proliferative (mild/moderate) retinopathy" (BR) and activates the radio button 21d.

In order to verify the selected preliminary diagnosis "background/non-proliferative (mild/moderate) retinopathy" (BR), the eye of the displayed picture 24 must comprise at least one of the lesions hemorrhages (HAEM), hard exudates (HE), and cotton wool spots (CWS). In order to further support the graders 6 to 8, each of the computers 1 to 3 is configured with a group of image processing algorithms in the present example. Each image-processing algorithm is designed to detect patterns related to a lesion which can appear in the eye. Examples of such patterns are fluffy white spots in the eye indicating cotton wool spots (CWS) and dark lines including dark spots indicating superficial intraretinal hemorrhages. Suitable image processing algorithms are pattern recognition algorithms which are notoriously known in the art. An example of such an image-processing algorithm is disclosed in G. Zahlmann, et al, "Hybrid Fuzzy Image Processing For Situation Assessment", IEEE Engineering In Medicine And Biology, January/February 2000, pp. 76-83.

In the present exemplary embodiment, the computer 1 activates automatically those image processing algorithms which are designed to detect patterns specific to hemorrhages (HAEM), hard exudates (HE), and cotton wool spots (CWS) and applies the image processing algorithms to the displayed picture 24, after the grader 6 selected the preliminary diagnosis "background/non-proliferative (mild/moderate) retinopathy" (BR) by activating the radio button 21d. In the present example, the image processing algorithms detect a fluffy white spot and dark lines including dark spots in the picture 24. The fluffy white spot is automatically surrounded by a rectangle 31 and the dark lines including dark spots are automatically marked by arrows 32 in the present embodiment. Detected patterns may also be colored, for instance.

Figure 4:
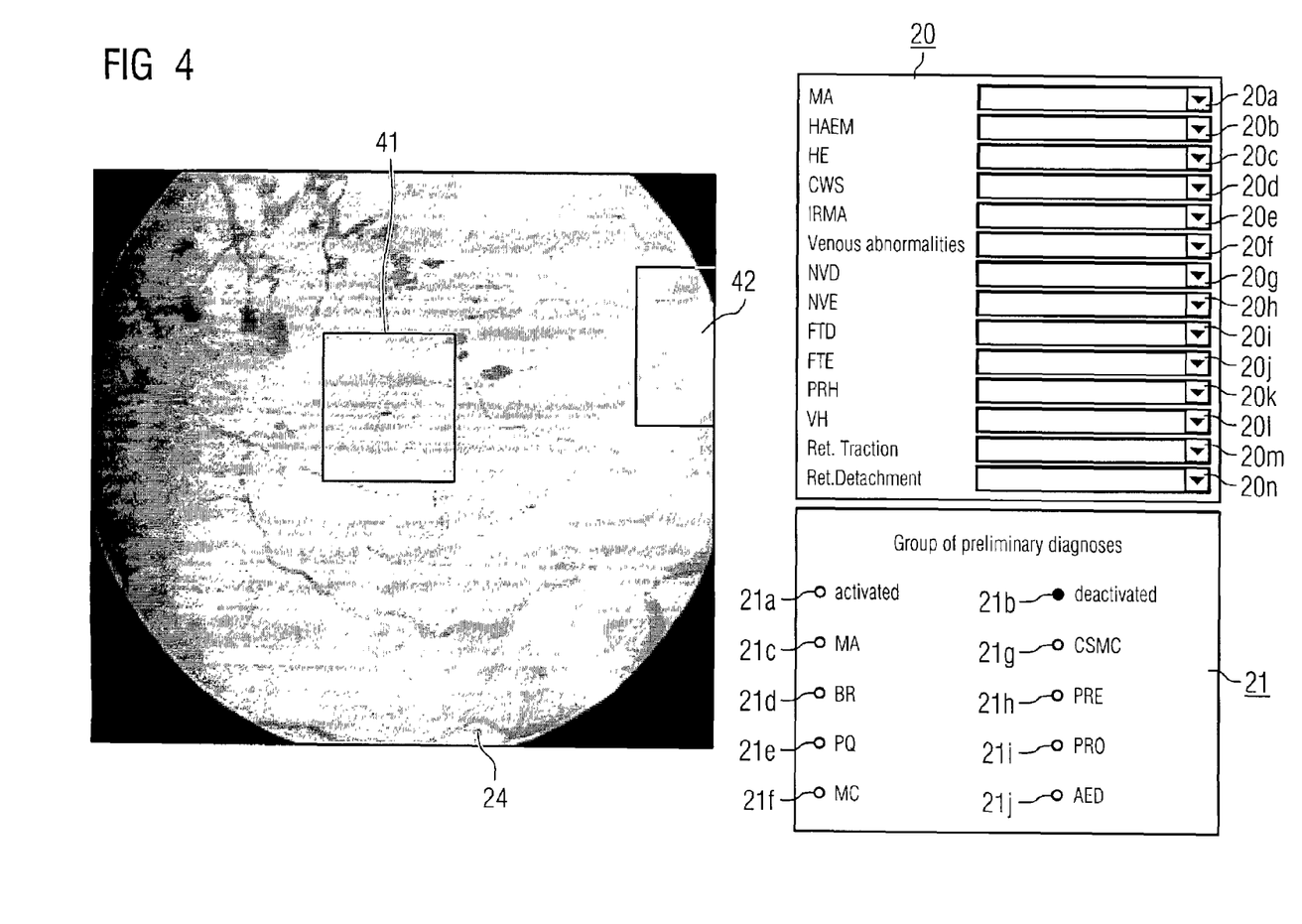

In the present example, the grader 7 is logged on the computer 2 during the operating mode. If she/he retrieves the picture 24 from the database 4, then the picture 24 is displayed on the screen 2a and the radio button 21b of the list 21 of the group of preliminary diagnoses is automatically activated in order to inactivate the list 21, as shown in FIG. 4. Since the grader 7 prefers to first evaluate the macula of a displayed eye, the computer 2 starts a further image-processing algorithm which is stored on each of the computers 1 to 3. This image-processing algorithm is designed to detect the macula of a displayed eye by searching for patterns specific to a displayed macula. After the image-processing algorithm detects the macula in the displayed picture 24, the computer 2 automatically surrounds the relevant region with a rectangular 41 in the picture 24 and zooms in the marked region. After the grader 7 evaluated the macula and documented her/his evaluation using the pull-down menus 20a to 20n of the list 20, the marked region of the macula is automatically zoomed out and removed from the picture 24. Then, the computer 2 starts a further image-processing algorithm which searches for a pattern which is related to the optic disk of an eye. After detecting that pattern, the computer 2 automatically marks the corresponding region 42.

Figure 5:
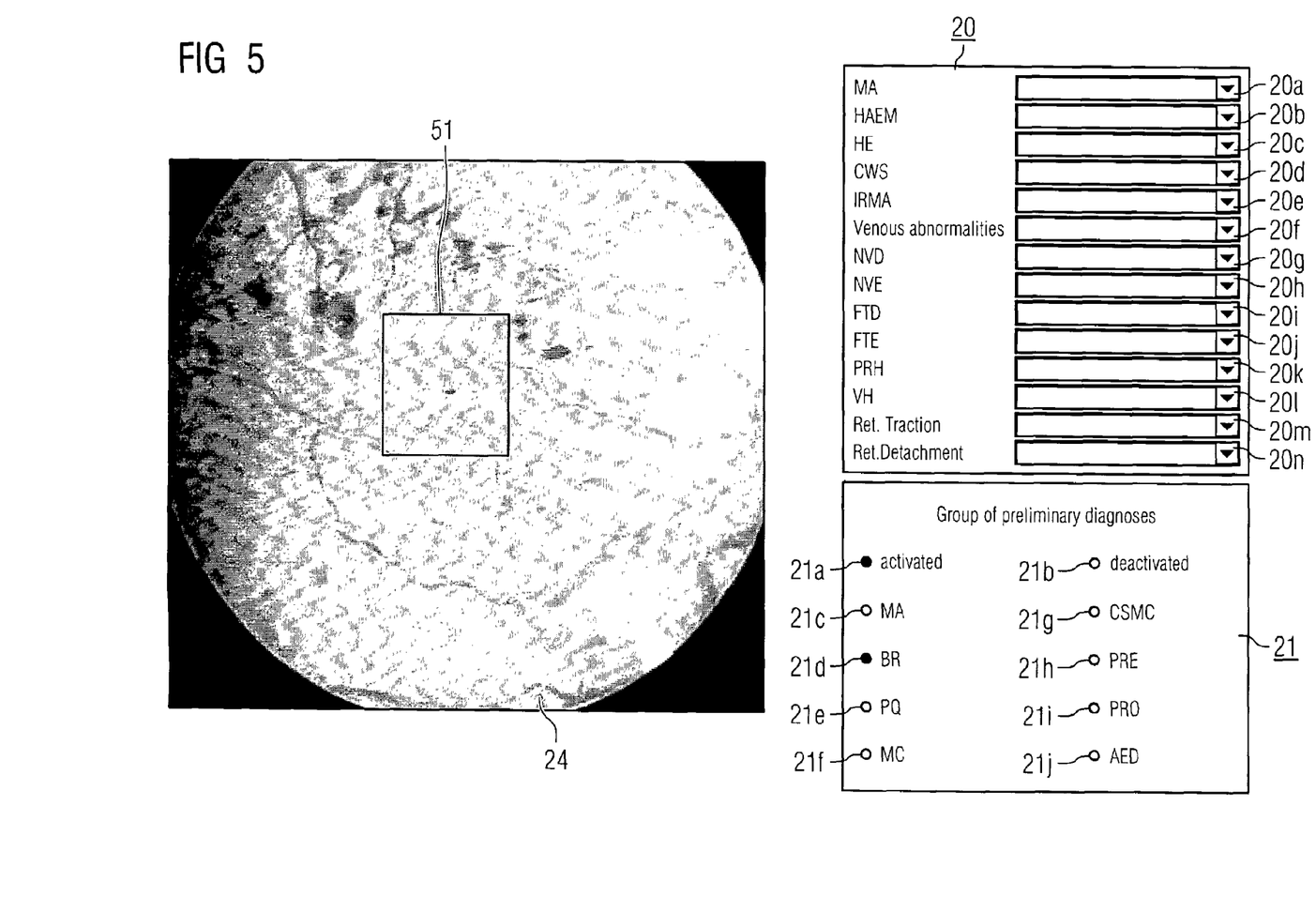

In the present example, the grader 8 is logged on the computer 3 during the operating mode. If she/he retrieves the picture 24 from the database 4, then the picture 24 is displayed on the screen 3a and the radio button 21a of the list 21 of the group of preliminary diagnoses is automatically activated, as shown in FIG. 5. After that, the grader 8 makes the preliminary diagnosis "background/non-proliferative (mild/moderate) retinopathy" (BR) and activates the radio button 21d.

Since the grader 8 prefers to first evaluate the macula of a displayed eye, the computer 3 starts the image-processing algorithm which detects the macula of a displayed eye. After the image processing algorithm detects the macula in the displayed picture 24, the computer 3 automatically surrounds the relevant region with a rectangular 51 in the picture 24 and zooms in the marked region After that, the computer 3 activates automatically those image processing algorithms which are designed to detect patterns specific to hemorrhages (HAEM), hard exudates (HE), and cotton wool spots (CWS) and applies the image processing algorithms to the zoomed in region of the displayed picture 24. In the present example, the image processing algorithms detect a dark spot, indicating hemorrhages (MAEM). The detected pattern is colored in the present example.

After the evaluation of the macula, the region comprising the macula is zoomed out and removed from the picture 24. Then, the image processing algorithms which are designed to detect patterns specific to hemorrhages (HAEM), hard exudates (HE), and cotton wool spots (CWS) are applied to the remaining picture 24 and detected patterns are highlighted.

Although modifications and changes may be suggested by those skilled in the art, it is the intention of the inventors to embody within the patent warranted hereon all changes and modifications as reasonably and properly come within the scope of their contribution to the art.

The invention claimed is:

1. A method for supporting an evaluation of a picture of an eye, comprising the steps of:
    displaying a picture of a patient's eye on a display screen;
    determining a series of regions of interest in said picture, said series of regions of interest being automatically selected without user intervention in response to predetermined eye evaluation preferences of a person selected from a plurality of persons who are evaluating said picture;
    subsequently marking on said screen each region of interest of said series of regions of interest in said picture on said screen; and
    manipulating said marked regions of interest on said display screen in response to said predetermined eye evaluation preferences.

2. The method of claim 1, comprising executing a computerized learning mode for determining said preferences for selecting said series of regions of interest.

3. The method of claim 1, comprising automatically surrounding at least one region of interest of said series of regions of interest with a frame wherein
    said eye evaluation references are associated with a preferred method of conducting an eye evaluation by a person.

4. The method of claim 1, comprising, for determining at least one region of interest of said series of regions of interest, the steps of:
    selecting an image-processing algorithm from a plurality of image processing algorithms;
        said selected image processing algorithm being designed to detect in said picture a pattern which is related to said at least one region of interest;
    applying said selected image processing algorithm to said picture; and
    marking a detected pattern on said screen as said at least one region of interest.

5. The method of claim 4, comprising emphasizing said detected pattern on said screen.

6. A method for supporting the evaluation of a picture of an eye, comprising the steps of:
    displaying a picture of a patient's eye on a screen;
    selecting an image processing algorithm from a plurality of image processing algorithms based on a preliminary diagnosis, selected from a plurality of diagnoses which are related to diabetes, each image processing algorithm of said plurality of image processing algorithms being associated with a diagnosis of said plurality of diagnoses and being designed to determine a series of regions of interest in said picture and for automatically selecting without user intervention said series of regions of interest in response to predetermined eye evaluation preferences of a person selected from a plurality of persons who evaluates said picture to search for a pattern which is specific to the respective diagnosis, said eye evaluation preferences being a with a preferred method of conducting an eye evaluation by a person;
    applying said selected image processing algorithm to said picture;
    marking a pattern on said screen which is detected by said selected image processing algorithm in said picture on said screen; and
    manipulating said marked regions of interest on said display screen in response to said predetermined eye evaluation preferences.

7. The method of claim 6, comprising emphasizing said detected pattern on said screen.

8. The method of claim 7, comprising automatically surrounding said detected pattern with a frame on said screen.

9. A system comprising:
    a database containing a plurality of pictures of the eyes of a plurality of diabetic patients;
    a display screen; and
    a data processing unit operatively coupled to said display screen and to said database configured to retrieve a picture selected from said plurality of pictures from said data base, display said retrieved picture on said screen, automatically determine without user intervention a series of regions of interest in said retrieved picture; said series of regions of interest being selected in response to predetermined eye evaluation preferences of a person selected from a plurality of persons who are evaluating pictures in said plurality of pictures, said eye evaluation preferences being associated with a preferred method of conducting an eye evaluation by a person, subsequently mark on said screen each region of interest of said series of regions of interest in said picture on said screen, and manipulate said marked regions of interest on said display screen in response to said predetermined eye evaluation references.

10. The system of claim 9, wherein data processing unit determines said preferences for selecting said series of regions of interest during a computerized learning mode.

11. The system of claim 9, wherein said data processing unit automatically surrounds at least one region of interest of said series of regions of interest with a frame on said screen.

12. The system of claim 9, wherein said data processing unit is further configured to:
    select an image processing algorithm from a plurality of image processing algorithms; said selected image processing algorithm being designed to detect a pattern which is related to at least one region of interest of said series of regions of interest, apply said selected image processing algorithm to said picture, and mark a detected pattern on said screen as said at least one region of interest.

13. The system of claim 12, wherein data processing unit emphasizes said detected pattern on said screen.

14. A system comprising:
a database containing a plurality of pictures of the eyes of a plurality of diabetic patients;
a display screen; and
a data processing unit operatively coupled to said screen and to said database and being configured to retrieve a picture selected from said plurality of pictures from said data base, display said retrieved picture on said screen, automatically determine without user intervention a series of regions of interest in said picture; said regions of interest being selected in response to predetermined eye evaluation preferences of a person selected from a plurality of persons who are evaluating said picture; select an image processing algorithm from a plurality of image processing algorithms; said selected image processing algorithm being designed to detect a pattern which is related to a preliminary diagnosis selected from a plurality of diagnoses and is related to said at least one region of interest, apply said selected image processing algorithm to said picture, mark a detected pattern on said screen in said retrieved picture on said screen, and manipulate said marked reions of interest on said display screen in response to said predetermined eve evaluation preferences.

15. The system of claim 14, wherein said data processing unit emphasizes said detected pattern.

16. The system of claim 14, wherein said data processing unit automatically surrounds said detected pattern by a frame on said screen.

* * * * *